United States Patent [19]

Liegeois

[11] 4,316,457
[45] Feb. 23, 1982

[54] PROCESS FOR PRODUCING ORTHOPEDIC STRUCTURES AND A THERMOPLASTIC LINEAR POLYURETHANE FOR USE IN SUCH PROCESS

[75] Inventor: Jean Marie C. G. Liegeois, Charneux-Herve, Belgium

[73] Assignee: Hexcel Corporation, San Francisco, Calif.

[21] Appl. No.: 195,370

[22] Filed: Oct. 9, 1980

Related U.S. Application Data

[63] Continuation of Ser. No. 1,261, Jan. 5, 1979, abandoned.

[30] Foreign Application Priority Data

Jun. 19, 1978 [EP] European Pat. Off. ............ 78100201

[51] Int. Cl.³ .............................................. A61L 15/00
[52] U.S. Cl. ................................. 128/156; 128/89 R; 128/90; 128/155; 427/2; 427/179; 427/246; 427/389.9; 427/392
[58] Field of Search ............... 427/177, 179, 243, 245, 427/246, 389.9, 439, 392, 393.5, 385.5, 2; 128/155, 156, 90, 89 R; 528/45, 80, 81

[56] References Cited

U.S. PATENT DOCUMENTS

| | | | |
|---|---|---|---|
| 3,551,364 | 12/1970 | McGarr | 427/389.9 |
| 3,891,785 | 6/1975 | Zemlin | 427/389.9 |
| 3,949,742 | 4/1976 | Nowakowski | 128/155 |
| 4,052,282 | 10/1977 | Kubushiro | 204/159.23 |
| 4,124,572 | 11/1978 | Mao | 528/80 X |
| 4,127,124 | 11/1978 | Clagett et al. | 128/156 |
| 4,131,114 | 12/1978 | Kirkpatrick et al. | 427/2 X |
| 4,143,665 | 3/1979 | Custer et al. | 128/90 |
| 4,156,067 | 5/1979 | Gould | 128/156 X |

Primary Examiner—Norman Morgenstern
Assistant Examiner—Thurman K. Page
Attorney, Agent, or Firm—John F. O'Flaherty; Lawrence Edelman

[57] ABSTRACT

A process for producing a rigid orthopedic cast in which a bandage material is provided which is impregnated or coated in the form of webs or sheets with a solvent solution of a polyurethane prepolymer, a bifunctional chain-extender and a catalyst. The prepolymer urethane having two isocyanate end groups, being formed by the reaction of a bifunctional compound reactive with an isocyanate group with a molar excess of a diisocyanate, forms a final thermoplastic polymer in the presence of the chain-extender when the solvent is removed under evaporative conditions. The heated thermoplastic impregnated fabric can be wrapped in multiple layers under normal conditions around a broken body member, molded and cooled to form a strong, rigid supportive cast which is porous so as to prevent skin maceration or other medical ramifications related to a non-porous material.

10 Claims, 1 Drawing Figure

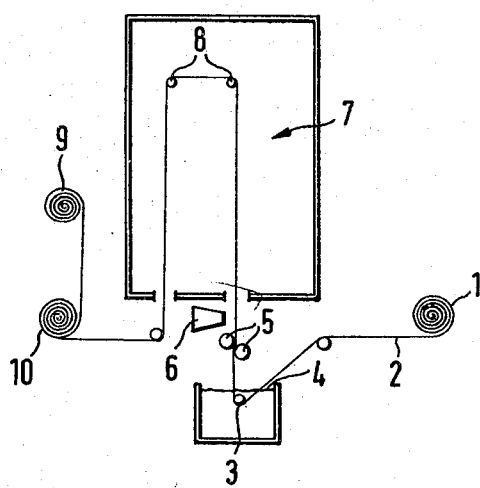

PROCESS FOR PRODUCING ORTHOPEDIC STRUCTURES AND A THERMOPLASTIC LINEAR POLYURETHANE FOR USE IN SUCH PROCESS

This is a continuation of application Ser. No. 001,261 filed Jan. 5, 1979 now abandoned.

This invention relates to a process for producing orthopedic structures such as tapes, bandages and supports, and to a new thermoplastic linear polyurethane, which is advantageously used for that process.

Orthopedic structures are commonly used in the fixation of ruptured bones, the immobilization of inflamed or injured joints, in case of disease or trauma and for the support and immobilization of ligamentous and muscular structures in cases of strains and sprains. In these orthopedic uses the immobilized limb may be encased in such rigid structure for long periods of time, frequently as much as six weeks or more.

Support splints may be used in case of paresis or weakness of muscles and as a correction means for deformities.

It has been known to use thermoplastic or thermosetting polymers as orthopedic cast materials.

In the U.S. Pat. No. 2,385,879 there is described an orthopedic cast material having strength and rigidity at room temperature and body temperature, which is readily moldable at higher temperature. This material comprises a copolymer of vinyl acetate and organic phosphate esters as a plasticizer.

From U.S. Pat. No. 2,853,067 there are known orthopedic casts, which are prepared by using a thermosetting resin, which is mixed with a catalyst and an accelerator.

According to U.S. Pat. No. 3,692,023 a polycaprolactone is used as a cast material employing permeable or porous base webs impregnated with the polymer.

These prior materials for forming splints, supports or bandages have, however, a number of inherent disadvantages. In some cases they are difficult to handle and discomfort the patient because of their too high shaping temperature. Materials containing toxic compounds such as plasticizers, monomers or catalysts, are liable to cause severe irritation and even inflammation of the skin.

Most of the prior processes for producing orthopedic structures involve processing of high molecular polymers and therefore the use of highly viscous solutions. As a consequence many process difficulties are caused and it is necessary to use highly diluted solutions and multistep impregnation processes for producing the bandages.

Concerning the above discussed state of the art a satisfactory cast material for orthopedic structures should be easy to handle and should not have properties which deleteriously affect the limb, particularly the skin.

The material should have a reasonable setting time or work life, should be free of offensive or noxious solvents or other chemicals and should set within a relatively short time under mild conditions.

After the cast or orthopedic structure is formed it should be of light weight, so as to minimize the inconvenience to the wearer, should be porous, should have sufficient structural strength and should be water-proof and as x-ray transparent as possible.

Despite of the characteristics of the cast it is highly desirable that the process for producing the orthopedic cast materials may be conducted in a simple and convenient manner without the necessity of handling highly viscous solutions.

The object of the present invention is therefore a new polymer for the use as an orthopedic cast material, which fulfils the above-mentioned prerequisites.

A further object of the present invention is a new process for producing orthopedic structures, which may be easily performed in a simple manner by using a highly concentrated solution of the polymer to impregnate the supports for the orthopedic structures.

The invention relates to a process for producing orthopedic structures, which comprises impregnating a fabric carrier with a solution of a polymer and removing the solvent from the impregnated carrier, which process is characterized in that the fabric carrier is impregnated with a solution in an organic solvent of a prepolymer polyurethane having two isocyanate end groups which has been formed by the reaction of a bifunctional compound reactive with an isocyanate group with a molar excess of a diisocyanate, which solution contains a chain extender and optionally a catalyst for the chain-extending reaction and the impregnated carrier is warmed to remove the solvent and to prepare the final polymer.

The invention also relates to the prepolymer and the thermoplastic linear polyurethane which is prepared by the above-described polymerisation of the prepolymer in situ in the impregnated fabric carrier. Regarding the overall procedure starting with the monomers until the formation of the final polymer, the polymer according to the invention is prepared by a two-step chemical synthesis. The first step comprises the reaction between a diisocyanate and an organic compound having two reactive hydrogen atoms in its end groups, which is preferably a diol, to form a prepolymer having two isocyanate end groups. The second step comprises the chain extension of the prepolymer by means of a usual bifunctional chain-extender.

The diisocyanate which is used for the first step may be any aromatic, aliphatic or cycloaliphatic diisocyanate, which is usually reacted to form polyurethanes. Representative examples for the diisocyanate are tetramethylene diisocyanate, hexamethylene diisocyanate, p-phenylene diisocyanate, p-toluylene diisocyanate, 4,4'-diphenyl-methane diisocyanate. Preferred are aliphatic and cycloaliphatic diisocyanates, such as hexamethylene diisocyanate, 4,4'-dicyclohexylmethane diisocyanate. If desired the reaction may be performed in the presence of usual catalysts, such as tertiary amines or tin compounds.

The bifunctional compound used as a starting material for the reaction with the above mentioned diisocyanate may be an oligomer having reactive end groups, such as OH—, NH—, $NH_2$—, COOH— or SH— groups. Examples for the bifunctional compounds are oligomers having two OH-end groups, such as polyethers, for example isotactic polypropylene oxide, polyurethanes, e.g. the oligomer obtained by the reaction of octamethylene diisocyanate and an excess of 1,3-butane diol, polyesters from aliphatic carboxylic acids and an excess of aliphatic diols, e.g. polytetramethylene sebacate, polyhexamethylene adipate. Other bifunctional compounds are polycarbonates, e.g. polytetramethylene carbonate, polyhexamethylene carbonate, polyamides having $NH_2$— or COOH—end groups, polysulfides, such as polytrimethylene disulfide.

Preferred oligomers are diols. Preferably the maximum molecular weight of those bifunctional compounds is about 10 000.

A preferred diol for the first step reaction with the diisocyanate is an oligomer of a cyclic lactone, such as δ-valero-lactone or alkyl-substituted δ-valerolactone, ε-caprolactone and a mono- or dialkyl-substituted ε-caprolactone, Ξ-enantolactone etc.

The cyclic lactone oligomer may be obtained by polymerization of the cyclic lactone in the presence of a usual starter for the ring cleavage of the lactone, such as the bifunctional compound of the general formula HY—R$_2$—ZH, in which R$_2$ is a lower alkylene radical, especially with 2 to 6 carbon atoms, and Y and Z are chosen among —S—, —O— and —NH—.

Commonly the starter will be an aliphatic diol from glycol to hexamethylene diol. The polymerization for forming the oligomer may be performed according to any usual procedure which is known in this field of the technique.

Preferably the oligomeric diol has a molecular weight of about 2000 to 6000.

In any case the bifunctional compound, especially the diol, is chosen in such a way that the final thermoplastic linear polyurethane prepared from the prepolymer has a fusion temperature lower than 80° C. In said first step generally n moles of a diol and n+1 moles of a diisocyanate are reacted in order to form the prepolymer. (n is the number of moles of the bifunctional compound, especially the diol, and may be about 1 to 5 and for the preferred case, where the bifunctional compound is a polylactone, it amounts to about 1 to 3, especially 1.)

The prepolymer obtained by the reaction of step 1 has two isocyanate end groups, which may be either free isocyanate groups or blocked isocyanate groups, which are blocked by usual blocking agents, such as phenol. In carrying out the reaction between the diisocyanate and the bifunctional compound, especially the diol, the lower the value of n, the higher the molecular weight of the diol, the maximum of which is about 10 000.

According to a preferred embodiment of the invention, there is prepared a new thermoplastic linear polyurethane by the above-described two-step reaction.

The first step comprises reacting an oligomer of a cyclic lactone of the formula

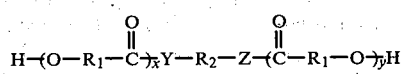

with a molar excess of a diisocyanate (which is defined above) of the formula OCN—R$_3$—NCO forming a prepolymer diisocyanate having recurring units of the formula

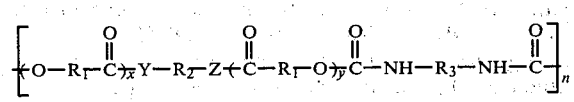

and two isocyanate end groups.

In the above formula R$_1$ represents an alkylene radical having 4 to 6 carbon atoms, preferably 5 carbon atoms, which is unsubstituted or may be substituted with lower alkyl groups, preferably with C$_1$ to C$_6$ and in particular with C$_1$ to C$_4$ alkyl groups, cycloalkyl groups, in particular cyclohexyl groups, lower alkoxy groups, in particular with 1 to 6 and preferably with 1 to 4 carbon atoms, the number of substituents being 1 to 3, R$_2$ is a lower alkylene radical having 2 to 6 carbon atoms, R$_3$ is the radical of an aromatic, aliphatic or cycloaliphatic diisocyanate, preferably a tetramethylene or hexamethylene radical, R$_1$ being identical radicals or mixed radicals, x and y being 0 to about 50, with the sum of x+y being comprised between about 25 to about 50, preferably 30-40, in particular about 34, x+y being chosen in such a way that the prepolymeric diisocyanate with one recurring unit of the above formula I has a reduced viscosity of less than 0.3 measured at a concentration of 0.2 g of the prepolymer in 100 ml benzene at 30° C.

Z and Y usually are O, S, NH or —COO—.

The second reaction comprises reacting the prepolymer obtained in step 1 with a bifunctional compound having two active hydrogen atoms which are apt to react with the isocyanate end groups of the prepolymer. This bifunctional compound may be chosen among the above-mentioned compounds for the first step reaction, preferably among the diols, and is either a low molecular weight compound, i.e. a monomeric compound, as commonly used for chain extension in the reaction of building up a polyurethane, or a higher molecular weight compound provided that it has a reduced viscosity below 0.3 as defined above, such as the oligomer polyactone used in step 1.

Preferred for the reaction of chain extension are diols, such as butane diol, hexane diol, or the above-stated oligomeric polylactone.

For the second reaction optionally a catalyst is used, which may be a tertiary amine or a tin compound, such as dibutyl tin dilaurate, which is usually known for the chain extension of prepolymer diisocyanates to form polyurethanes. This catalyst is used in the usual concentration for this reaction.

The final thermoplastic linear polyurethane, which is formed by the chain-extending reaction between the prepolymeric diisocyanate and the diol, is a material having a molecular weight of about 25 000 to 80 000, usually about 40-45 000.

If the thermoplastic polyurethane according to the invention is used for the production of orthopedic cast forming material in the form of a bandage, web, film, tape or sheet, the second reaction, i.e. the reaction of chain extension is performed while the prepolymer, which is in form of a solution in a usual solvent, preferably an aliphatic ketone, is impregnated in a usual fabric carrier for orthopedic tapes or sheets. That means that firstly the fabric carrier is impregnated with a solution in a usual solvent, comprising the prepolymer and the diol, which contains optionally a catalyst, a pigment or dye, and then it is heated at temperatures of from about 50°-160° C., whereby the solvent is evaporated and the chain extension takes place to form the final polymer. If the polymer according to the invention is used for the production of orthopedic splints or supports, the prepolymer and the diol are mixed with a usual pigment or dye, optionally an inert filler and optionally a catalyst and the mixture is cast into molds or formed by extrusion.

The orthopedic casts according to the invention may be in the form of sheets, tapes and preformed contour-fitting shapes for the application to the human or animal body. In this case, there is used a base- or support material as a carrier for the polymer, which may be a flexible fabric web, which has preferably relatively large openings and relatively heavy strands.

Preferably the strands are of a loose weave or knit, so as to be porous and subject to at least partial impregnation by the polymeric material. The web carrier serves as a structural element in the final product and is coated with the polymeric composition.

The carrier material is preferably a flexible large mesh fabric preferably knit defining a lattice or relatively large openings. The smallest dimension of the openings may generally be at least 0.097 $cm^2$ and preferably a minimum of 0.142 $cm^2$ about 0.219 $cm^2$ and generally not exceeding 1.613 $cm^2$, more usually not exceeding 0.323 $cm^2$. The openings may be of any configuration, such as square, polgonal, or the like. The opening shall be large enough so that in the finished product the polymer composition preferably does not form air impervious windows across the openings.

The strands of the carrier which define the openings are preferably formed of relatively coarse, bulky, staple, porous, low density and thermal insulating material such as heavy yarn of 5 to 15 twist and having a raw diameter of at least 0.330 mm preferably about 0.381 mm and generally not exceeding 1.016 mm and when incuding the fluff or fuzz around the yarn strands at least 0.762 mm, preferably a minimum of 1.270 mm, about 1.905 mm and generally not exceeding 5.080 mm and more usually not exceeding 2.540 mm.

Materials which may be used include cellulosic materials, such as cotton, synthetic materials, such as acrylates and nylon, or combinations thereof. For the most part, organic materials are employed, rather than more thermal conductive inorganic materials, such as glass fibers. Some significant factors concerning the material are that the material be a thermal insulator, that it provide structural stability to the final product, that it allow for molding to form the orthopedic structure, that it is wettable by the polymer composition, and that it is stable under normal usage. By way of more specific example, the low density strands of bulky Raschael type knits formed of staple fibers of cotton and defining naturally occurring multitudious voids provides a desirable carrier material. A knit of the Raschael type inherently provides a highly flexible carrier material.

Preferably, the material should be substantially free of additives which may interfere with the bond between the polymer and the fiber. Cellulosic materials are preferably scoured to remove any binders or lubricants inhibiting the wetting properties of the polymer or other possibly deleterious additives.

In the following a practical process for the production of an orthopedic cast-forming bandage will be described in detail. The polymer composition, comprising the prepolymer having two free or blocked isocyanate-end groups, and the chain-extender, preferably a diol, are mixed with an inert, volatile solvent, such as an aliphatic ketone, optionally a pigment or dye which is usually employed for pigmenting of polyurethanes, such as titanium dioxide, and optionally the catalyst.

A suitable viscosity of the mixture may be set by appropriate choice of the ratio of polymer to solvent.

As the viscosity of the prepolymer according to the invention is low, it is not necessary to use large amounts of solvent for preparing the impregnating solution.

The pigment may be used in small amounts, generally not exceeding 15% by weight, ore usually not exceeding 10% by weight, and preferably from about 3 to 8% by weight.

BRIEF DESCRIPTION OF THE DRAWING

The sole FIGURE relates to an apparatus suitable for the preferred embodiment in the process of the present invention.

DESCRIPTION OF THE PREFERRED EMBODIMENTS

A preferred embodiment of the process for impregnating the fabric carrier and subsequent reaction of chain extension is now described by reference to the attached figure.

According to the figure a roll 1 of the appropriate knitted or loose carrier woven webbing 2 is provided. The webbing 2 is passed under tank roller 13 and immersed in coating solution 4.

The initially coated webbing is then passed between adjustable trunnion rolls 5 and past an air knife 6 and thence circuitously through oven 7 passing over rollers 8 adjacent the upper regions of the oven 7. The air knife 6 serves to blow out any polymer windows which may have formed in passing through the wet polymer solution 4, and the air knife also assists in the drying of the polymer applied to the wet carrier 3. The webbing in passing through the drying oven 7 is dried at an elevated temperature.

As the prepolymer solution, which is used according to the invention for impregnating the fabric, has a relatively low viscosity, the fabric is not only coated, but impregnated with a prepolymer throughout its structure. During the passage of the webbing through the drying oven 7 the solvent is evaporated, the blocking groups of the isocyanate groups, if there have been used any, are removed and the reaction of chain extension proceeds to form the final thermoplastic linear polymer within the structure of the webbing.

A release film of polyethylene or similar material from an unwind roll 9 may be employed in forming the take-up roll 10 of the impregnated web 2 if the roller bandage layers adhere to each other during rolling or when the roll is heated to working temperature prior to its use in the making of an orthopedic cast as more specifically described hereinafter.

In the preferred embodiment the diameter of the impregnated strands of the web 2 were measured in the range of between approximately 0.254 mm to 6.604 mm and generally between 1.905 mm and 4.064 mm.

The size of the openings of the impregnated web should generally be in a somewhat lower range of areas than given previously with respect to the dimension of the openings of the unimpregnated carrier material.

The smallest dimension of the coated opening will generally be at least 0.065 $cm^2$, preferably a minimum of 0.129 $cm^2$, about 0.168 $cm^2$, generally not exceeding 1.613 $cm^2$ and usually not exceeding 0.323 $cm^2$. The shape of the openings shown in the impregnated web are disclosed as being in the form of a non-rectangular parallelogram as distinguished from the near square shaped openings of the unimpregnated knit carrier. Such variation in shape between the uncoated and coated carrier may result from the manner in which the carrier is handled during the coating process. In manufacturing the impregnated web according to the process described in reference to the figure and without utilizing rather special web tracking and handling equipment, it was found that the web could be better handled through the impregnation and oven drying process by running the fabric with the strands oriented parallel and perpendicular to the line of travel of the material through the equipment. Where the carrier material is originally oriented in a diagonal direction with respect to the strands, it may be desirable to cut the material on a bias and run it through the coating process so that the strands are substantially parallel and perpendicular instead of diagonal to the line of travel. Such an orientation will give a more rectangular finished product.

However, the orientation during coating is not important and in order to provide an entirely satisfactory bandage it is not necessary that the openings be square or rectangular. It is important, however, that the openings after coating be of substantial area ranging for example between not less than 0.065 cm$^2$ to not more than 1.613 cm$^2$ and more preferably between 0.129 cm$^2$ and 0.323 cm$^2$ and around 0.168 cm$^2$.

As earlier noted it is important that the openings be large enough so that when a cast is formed by spirally wrapping and overlapping the material around the injured limb, that air passages through the thickness of the cast will be maintained to permit the underlying skin of the patient to breathe and to permit volatilization and dissipation of moisture from the interior of the cast.

In the process of forming an orthopedic splint or support the prepolymer having two blocked or free isocyanate-end groups is usually mixed with the chain extending agent, i.e. the above-described diol, and optionally with a pigment or dye, optionally a catalyst for the chain extending reaction and optionally a usual filler, which must be inert and essentially moisture-free. A specific example for such a filler is talc, and other compounds with spherolitic or lamellar structure such as precipitated calcium carbonate or $SiO_2.Al_2O_3$ with or without a usual surface treatment. The mixture may be formed by usual shaping processes and equipments, such as by casting or extrusion, provided that there is maintained a residence time and temperature, sufficient for the complete proceeding of the chain-extending reaction.

The orthopedic cast- or sheet material, which has been obtained according to the described procedure, can be formed in rolls which may be warmed above the softening temperature of the resin. The thermally softened impregnated fabric becomes highly flexible and pliant and may then be wrapped in multiple layers about the limb to be immobilized. The large knit fabric carrier allows for twisting of the fabric, forming and reforming, so as to obtain the desired shape and degree of support. The overlapping layers of impregnated fabric bond to each other during wrapping and whereafter the impregnated fabric rapidly cools to a hard structurally stable cast, which is porous so as to minimize maceration or other deleterious skin conditions from developing.

The formed orthopedic cast is light and stable under normal usage conditions, is moisture-proof and lightweight. The cast is easily removed by utilizing conventional cast-cutting or sawing techniques and equipments.

A particular advantage of the orthopedic cast material is the fact that the polymer is impregnated throughout the structure of the textile carrier, which in turn causes an improved strength of the product and avoids the filling of the openings of the web by polymer.

The splints according to the invention are of high strength and stability at room and body temperature and do not release noxious substances.

The use of the prepolymer according to the invention to impregnate the carrier of the tape or sheet also leads to important advantages compared with the prior techniques. As the prepolymer has a lower viscosity, the impregnation of the carrier may be attained with a more concentrated solution and by using a much less amount of solvent, compared with the prior process for impregnating the carrier. According to the invention only 1/20 to 1/25 of the amount of the solvent is required. Therefore, there are important savings of solvent and less polution of the environment when evaporating the solvent. As the concentration of solids in the impregnating solution is higher, a one-step impregnation is sufficient to obtain the required amount of polymer in the final structure.

Further according to the invention it is possible to use solvents, such as ketones, having lower toxicity, while according to the prior art the use of methylene chloride has been necessary.

In the following the invention is further explained by examples.

The melting points of the polymers stated in the examples have been measured by differential scanning calorimetry. The intrinsic viscosities have been measured under the conditions which are explained in example 1.

EXAMPLE 1

704.1 gr. of a epsilon caprolactone oligomeric diol of molecular weight about 3000, reduced viscosity at 0.2 gr in 100 ml benzene at 30° C. of 0.11, has been added to 248.8 gr of methyl ethyl ketone (MEK) previously dried with a 3 angstroem molecular sieve, in a 1.5 liter stirred glass reactor. After mixing has been achieved, 119.77 gr of 4,4'-diphenylmethane diisocyanate (MDI) have been added and the reacting mixture maintained under a dried nitrogen blanket. By water circulation in the jacket the temperature has been raised to 60° C. and the mixture has been kept under mixing for several hours after what 43.63 gr of phenol have been added to the system maintained at the same temperature. After complete reaction two mixtures have been prepared. One mixture containing 488.36 gr of the prepolymer solution and 9.68 gr of butane diol-1,4 and 11.55 gr of titanium dioxide placed in the oven at 160° C. produced a polymer of melting point 49° C. and intrinsic viscosity in tetrahydrofuran (THF) at 25° C. of 0.775.

The other mixture containing 563.01 gr of the prepolymer solution, 375.38 gr of the same diol as the one used to prepare the prepolymer, 440 gr of dried MEK, 23.4 gr of titanium dioxide had a viscosity of 280 centipoises as measured with a Brookfield viscometer at 40° C. This mixture has been used to impregnate successfully a cotton cloth with wide openings, then hung in the oven at 160° C. The polymer on the substrate had an intrinsic viscosity of 0.58. After immersion in hot water, the resulting composite material is suitable to prepare self adherent bandage that hardens under cooling.

EXAMPLE 2

Using the same equipment, the same procedure and the same reagents as described in example 1, a prepolymer solution has been made from a reaction mixture containing 775 gr of diol, 131.3 gr of MDI and 454.48 gr of MEK. After complete reaction which took place at 70° C., 47.18 gr of phenol have been added and allowed to react further. A mixture has been made with 300 gr of the prepolymer solution, 164.91 gr of the same diol as the one used to prepare the prepolymer, amount representing an equimolar ratio, 82.4 gr of dried MEK. This mixture with a low content of solvent had a viscosity of 600 centipoises at 40° C. An aliquot cast in the oven at 160° C., produced a polymer of intrinsic viscosity 0.62. An other aliquot to which 3.3 percent of titanium dioxide had been added was used successfully to impregnate a cotton cloth with wide openings. The resin then produced in the same conditions had a melting point of 53.5° C. Kept four days at 40° C. in contact with the atmosphere, the mixture described above had no large increase of viscosity. A cast made after six days in the oven at 160° C. still produced a polymer of intrinsic viscosity 0.62.

EXAMPLE 3

Using the same equipment and the same procedure as in example 1, a prepolymer solution has been made from 78.55 of MDI, 492.86 gr of dried MEK, and 625.28 gr of an epsilon caprolactone oligomeric diol of molecular weight about 4000, reduced viscosity at 0.2 gr in 100 ml of benzene at 30° C. of 0.15. The reaction took place at 70° C. with 2.2 ml of N,N,N′,N′-tetramethyl-1,3-diaminobutane as catalyst. After complete reaction, 32.89 gr of phenol have been added and allowed to react further. 1.08 gr of hexane diol has been mixed with 60.45 gr of the prepolymer solution; the mixture cast in the oven at 160° C. produced a polymer of melting point 54° C. and intrinsic viscosity 0.63.

EXAMPLE 4

Using the same equipment, the same procedure and the same reagents as in example 3, a prepolymer solution has been made from 707.70 gr of diol, 88.4 gr of MDI and 555.5 gr of dried MEK. After complete reaction at 60° C., 37.86 gr of phenol have been added and 2.0 ml of N,N,N′,N′-tetramethyl-1:3-diaminobutane thereafter. A mixture containing 29.93 gr of the prepolymer solution and 0.40 gr of diethyleneglycol has been cast in the oven at 160° C. and produced a polymer of melting point 53° C. and intrinsic viscosity 0.49. The same mixture containing 3 percent titanium dioxide produced in the same conditions a polymer with a melting point of 54° C. Another mixture containing 38.76 gr of prepolymer solution and 0.296 gr of ethylenediamine produced in the same conditions, a polymer with a melting point of 56° C., and the latter mixture with 3 percent of titanium dioxide gave a withe product with a melting point of 55° C. A mixture containing 455.14 gr of the prepolymer solution, 161.71 gr of dried MEK, 231.05 gr of the diol used to prepare the prepolymer and 24.55 gr of titanium dioxide had a viscosity of 650 centipoises at 50° C. and has been used successfully to impregnate a cotton cloth with wide openings leading after oven treatment at 160° C. to a composite material able to form resistant orthopedic bandages. The melting point of the resin on the substrate was 53° C.

EXAMPLE 5

Using the same equipment and the same procedure as in example 1 a prepolymer solution has been made from 508.69 gr of an epsilon caprolactone oligomeric diol of molecular weight 4000, reduced viscosity at 0.2 gr in 100 ml of benzene at 30° C. of 0.15, 276.02 gr of dried MEK and 42.83 gr. of hexamethylenediisocyanate 1-6. After formation of the prepolymer whose reduced viscosity was 0.24, 150.22 gr of the prepolymer solution was added to 2.08 gr of butane diol 1-4, placed in the oven at 140° C. to produce a polymer of melting point 58° C. and intrinsic viscosity 1.34. 70.69 gr of the prepolymer solution and 1.15 gr of diethyleneglycol were treated in the same way and produced a polymer with a melting point of 57° C. and an intrinsic viscosity of 1.15. In the same conditions 61.75 gr of the prepolymer solution and 1.43 gr triethyleneglycol have a polymer of melting point 56.5° C. and intrinsic viscosity 1.00, while 71.60 gr of the prepolymer solution and 1.30 gr of hexanediol 1-6 gave a polymer with a melting point of 56° C. and an intrinsic viscosity of 1.51.

EXAMPLE 6

Using the same equipment and the same procedure as in example 1 a prepolymer solution has been made by reaction of 790.73 gr of an epsilon caprolactone oligomeric diol of molecular weight about 4000, reduced viscosity at 0.2 gr in 100 ml of benzene at 30° C. of 0.15, with 103.85 gr of dicyclohexylmethane diisocyanate in 625.15 gr of dried MEK. After complete reaction 94.62 gr of the prepolymer solution has been mixed with 1.13 gr of butanediol 1-4, cast in the oven at 140° C. to produce a polymer of melting point 56° C. and intrinsic viscosity of 0.76. The same mixture with 3 percent of titanium dioxide gave a polymer of melting point 59° C. A mixture made of 92.90 gr of the prepolymer solution and 1.83 gr of triethyleneglycol produced in the same conditions a polymer with a melting point of 54° C. and an intrinsic viscosity of 0.65.

EXAMPLE 7

Using the same equipment, the same procedure and the same reagents as in example 6, a prepolymer solution has been made with 822.51 gr of diol, 108.03 gr of dicyclohexylmethanediisocyanate and 654.03 gr of dried MEK, with in addition, 0.2 m of dibutylindilaurate as catalyst. After complete reaction, a mixture made of 250.91 gr of the prepolymer solution, 130.50 gr of the same diol as the one used to prepare the prepolymer, 179.03 gr of dried MEK and 13.90 gr of titanium dioxide, having a viscosity of 120 centipoises at 25° C. has been used successfully to impregnate a cotton cloth with wide openings. After treatment in the oven at 140° C., the obtained composite material was suitable for orthopedic applications. The melting point of the resin was 52° C. and its intrinsic viscosity was 0.84.

EXAMPLE 8

In a one liter glass stirred reactor, 54.5 gr of 4,4′-diphenyl methanediisocyanate have been added, without solvent to 416.71 gr of an epsilon caprolactone oligomeric diol of molecular weight about 4000, reduced viscosity at 0.2 gr in 100 ml benzene at 30° C. of 0.15. Water circulation in the jacket allowed to control the reaction temperature at 80° C. After complete reaction, a mixture has been made with 406.1 gr of prepolymer and 359.36 gr of the same diol as the one used to prepare the prepolymer and divided into four parts. One part has been placed in the brabender plastograph acting batchwise in the same way as an extruder would act continuously. A continuous increase of the reacting torque was found indicating the formation of the polymer whose final intrinsic viscosity was 1.26. A sheet of 3 mm thickness has been molded in the press giving a suitable material for splint application. The shear modulus of this material at 23° C. is 880 kg/cm$^2$ and the tensile modulus is 3090 kg/cm$^2$. The three other parts have been mixed respectively with 10, 15, and 20 percent of talc as filler, cast in molds and placed in the oven at 120° C. The fairly low viscosity of the mixture as prepared allows a rapid mixing of the filler with low energy requirements. The polymer formed in the first material had an intrinsic viscosity of 1.31. Sheets of 3 mm thickness has been prepared in the press with these materials giving respectively with the increase of filler content: 1274, 1326 and 1394 kg/cm² for the shear modulus at 23° C., and 2672, 3553 and 3198 kg/cm² for the tensile modulus at the same temperature. The increase of shear modulus due to the filler is of interest for splint applications, as well as the fact that the sheet can be shaped after immersion in hot water being then also self adherent.

I claim:

1. A process for producing rigid orthopedic structures which comprises impregnating a pliant fabric material with a solution comprising the group consisting of a polyurethane prepolymer, a chain extender, and solvent and removing the solvent from the impregnated carrier, characterized in that the fabric material is impregnated with a solution in an organic solvent of a prepolymeric polyurethane having two isocyanate end groups, which has been formed by the reaction of an oligomeric diol with a molar excess of a diisocyanate such that the diol to diisocyanate ratio is n:n+1, where n=1 to 5, which solution contains a bifunctional chain-extender and the impregnated material carrier is heated to remove the solvent and to prepare the final thermoplastic linear polymer in situ.

2. The process according to claim 1, characterized in that the organic solvent is an aliphatic ketone.

3. The process according to claim 1 or 2, characterized in that the prepolymeric polyurethane has been formed by the reaction of n moles of a diol and n+1 moles of a diisocyanate, where n is 1 to 3.

4. The process according to one of claims 1 to 3, characterized in that the diol is an oligomeric diol of the formula

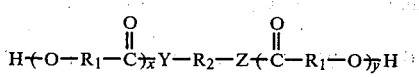

wherein $R_1$ represents an alkylene radical having 4 to 6 carbon atoms, which is unsubstituted or may be substituted with lower alkyl groups, cycloalkyl groups, lower alkoxy groups, the number of substituents being 1 to 3, the radicals $R_1$ being identical radicals or mixed radicals, $R_2$ represents a lower alkylene radical having 2 to 6 carbon atoms, Y and Z comprise the group consisting of —O—, —NH— or —COO—, and x and y are 10 to 20.

5. A bandage material for forming in place a rigid orthopedic cast, comprising a pliant fabric material comprising low density strands of relatively bulky heat insulating material and defining openings of relatively large diameter; each strand being coated and at least partially impregnated with a solvent solution of a polymer composition comprising a prepolymeric polyurethane having two isocyanate end groups, a chain-extender, and a solvent wherein the solvent is removed under evaporation conditions in the presence of the pliant fabric such that the final thermoplastic linear polyurethane is formed in situ, comprising recurring units of the prepolymeric polyurethane which are linked by radicals of a bifunctional chain-extender, characterized in that the prepolymeric polyurethane is formed by reacting a diol of the general formula

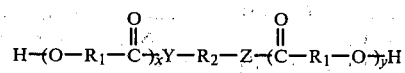

with a diisocyanate of the general formula $OCN-R_3-NCO$, wherein $R_1$ represents an alkylene radical having 4 to 6 carbon atoms, which is unsubstituted or may be substituted with lower alkyl groups, cycloalkyl groups, lower alkoxy groups, the numer of substituents being 1 to 3, the radicals $R_1$ being identical radicals or mixed radicals, $R_2$ represents a lower alkylene radical having 2 to 6 carbon atoms, $R_3$ comprising the group consisting of a radical of an aromatic or aliphatic diisocyanate, and Y and Z comprise the group of —O—, —NH— or —COO—, x and y are 10 to 20.

6. A bandage material according to claim 5, wherein the area of the openings is not less than 0.015 cm² and not greater than 1.613 cm².

7. A bandage material according to claim 5 wherein the area of the openings is not less than about 0.129 cm² and not greater than about 0.323 cm².

8. A bandage material according to claim 5, wherein the openings are approximately 0.168 cm².

9. A bandage according to claim 5 wherein said carrier comprises a Raschael type substantially cotton knit of staple fiber bulky strands.

10. The process according to claim 1 wherein the solvent is removed under evaporative conditions such that the polyurethane prepolymer, and chain-extender diol form the final thermoplastic polyurethane coated on and impregnated throughout the pliant fabric material carrier.

* * * * *